US005762949A

United States Patent [19]

Kern

[11] Patent Number: 5,762,949

[45] Date of Patent: *Jun. 9, 1998

[54] FORMULATION AND PROCESS FOR CONTROLLING ISOPTERA INSECTS

[75] Inventor: Manfred Kern, Lörzweiler, Germany

[73] Assignee: Hoechst Schering AgrEvo GmbH, Berlin, Germany

[ * ] Notice: The term of this patent shall not extend beyond the expiration date of Pat. No. 5,573,770.

[21] Appl. No.: 694,483

[22] Filed: Aug. 7, 1996

Related U.S. Application Data

[62] Division of Ser. No. 381,701, Jan. 31, 1995, Pat. No. 5,573,770.

[30] Foreign Application Priority Data

Feb. 20, 1994 [DE] Germany ............ 44 03 062.2

[51] Int. Cl.⁶ .................................. A01N 25/086
[52] U.S. Cl. .................. 424/405; 424/408; 424/409
[58] Field of Search ............ 424/409, 405, 424/408

[56] References Cited

U.S. PATENT DOCUMENTS

| | | | |
|---|---|---|---|
| 3,853,346 | 12/1974 | Bailey | 43/124 |
| 4,845,103 | 7/1989 | Spaulding et al. | |
| 4,851,218 | 7/1989 | Hildebrandt et al. | |
| 4,864,027 | 9/1989 | Shubert et al. | |
| 4,990,514 | 2/1991 | Bruey | |
| 5,024,832 | 6/1991 | Omatta et al. | 424/84 |
| 5,288,727 | 2/1994 | Toki et al. | |
| 5,553,770 | 9/1996 | Kern | 424/405 |

FOREIGN PATENT DOCUMENTS

WO 92/14363   9/1992   WIPO .

OTHER PUBLICATIONS

J. Appln. Ent. 113 (1992), pp. 466–471 by J.K. Grace et al. entitled "Laboratory evaluation of the novel soil insecticide silafluofen against Coptotermes formosanus Shiraki".

Chemical Patents Index, Basic Abstracts Journal, Derwent Publications Ltd., Abstract No. 87–180602.

Chemical Patents Index, Documentation Abstracts Journal, Derwent Publications Ltd., Abstract No. 90–111917.

Chemical Patents Index, Documentation Abstracts, Journal, Derwent Publications Ltd., Abstract No. 93–339598.

Pesticide Science, 1990, pp. 289–307, by Sieburth et al., entitled Organsilane Insecticides, Part I: Biological and Physical Effects of Isosteric Replacement of Silicon for Carbon in Etofenprox and MTI–800.

Kerkut and Gilbert, Comprehensive Insect Physiology, Biochemistry and Pharmacology, vol. 2, Postembryonic Development, Pergamon Press, 1985, pp. 73, 74.

*Primary Examiner*—Thurman K. Page
*Attorney, Agent, or Firm*—Curtis, Morris & Safford, P.C.

[57] ABSTRACT

The invention relates to formulations comprising silafluofen for controlling social insects, and to a process for controlling them, in which the insect populations are destroyed using acutely sublethal doses of silafluofen.

20 Claims, No Drawings

FORMULATION AND PROCESS FOR CONTROLLING ISOPTERA INSECTS

This application is a division of application Ser. No. 08/381,701, filed Jan. 31, 1995 now U.S. Pat. No. 5,573,770.

The invention relates to formulations which comprise silafluofen for controlling social insects, and to a process for controlling them, in which the insect populations are destroyed using acutely sublethal dosage rates of silafluofen.

The two most important passive processes for controlling insects are traps and toxic baits. In order to be active, both types must comprise a component which attracts the insects. An attractant for wasps is described, for example, in U.S. Pat. No. 4,851,218. Traditional insect traps, be it sugar water in a container or fly paper coated with an adhesive, only act on individuals which have been attracted.

Toxic preparations can be formulated using insecticides with a variety of actions, and there exist two main principles of action which can be distinguished: rapid action and delayed action.

Rapidly acting insecticides which destroy the insects immediately after the insects have come into contact with them or have ingested food, are suitable for controlling non-colony-forming insects. These insecticides are generally employed as aerosols or in the form of sprays. They are most easily used in the form of aqueous, partly aqueous or non aqueous formulations.

Insecticides with a delayed action are suitable for a different type of insect, i.e. for the so-called social or colony-forming insects. For example, the activity of pesticides with a delayed action may be due to the toxic moiety of a molecule being released slowly. Other methods for the delayed release of active substances are the use of semipermeable membranes, microencapsulation or binding the active substances to polymers. Insecticides which engage in the metabolism of insects and which interrupt vital processes may also result in destroying the insects with a time lag. Yet another type of insecticides, with a delayed action is the type which has a rapid action at high concentrations, i.e. which is acutely lethal, but which, when applied at a lower, so-called acutely sublethal dosage rate, only destroys the insects after these smaller amounts of the active substance have been ingested repeatedly and involves a time lag.

The social insects include the ants, termites, wasps and bees, but there are also non-colony-forming species in the case of the wasps and bees. The term "social insects" is used to describe those insect species in which all progeny of a female (queen) or of several females coexist in nests (insect colonies) characterized by strict division of labor. Rapidly destroying single individuals has no-effect on the nest. However, if a substance with a delayed action is mixed, for example with a bait, the individuals which gather food will transport this formulation to the nest where it is distributed to larvae, workers and the queen. If a sufficient quantity of active substance has been transported back to the nest, the entire colony can be destroyed in the course of 1 to 2 weeks by such feed substitution. In order to ensure that a sufficient quantity of active substance is carried back to the nest, the active substance formulation intended to attract the insects must not have an insect-repellant action. It should furthermore be protected against degradation.

A number of active substance formulations with a delayed action and their use in the control of social insects is already known. For example, WO 92/14363 describes aqueous formulations of perfluoroalkanesulfonates for the control in particular of wasps. Pages 3 to 6 in this publication feature an extensive discussion of the advantages and shortcomings of other prior-art formulations with a delayed action in the control of social insects.

Surprisingly, it has now been found that 4-etoxyphenyl [3-(4-fluoro-3-phenoxyphenyl)propyl]dimethylsilane (≈silafluofen) has sufficiently low contact action that acutely sublethal doses are picked up by wasps and other social insects in a suitable feed and transported into the nest, where it displays a "hive-systemic" activity, with the consequence that the other inhabitants of the nest or hive are destroyed at a later point in time.

The invention therefore relates to insecticidal formulations for controlling social insects, which comprise silafluofen and a suitable carrier, the silafluofen content being such that the formulation has no acutely lethal action on those individuals by which it is picked up, and to a process for controlling social insects, in which a formulation comprising silafluofen is placed at a site which is accessible to the insects and frequently visited by them, the insects pick up the formulation, transport it to their nest and, if appropriate, feed it to other individuals, the silafluofen content being such that the formulation, after a time lag, destroys the individuals which have picked up the formulation directly and/or have taken it up by feeding.

Silafluofen and processes for its preparation are disclosed is U.S. Pat. No. 4,864,027. Formulations comprising this active substance are described, inter alia, in EP-A-443412.

Social insects are to be understood as meaning colony-forming species from the Hymenoptera families and super families Formicidae Apoidea and Vespoidea, and species from the order Isoptera The abovementioned insect includes:

From the order of the Isoptera the families Mastotermitidae, Kalotermitidae, Hodotermitidae (in particular Hodotermitinae, Termopsinae), Rhinotermitidae (in particular Coptotermitinae, Heterotermitinae, Psammotermitinae), Termitidae (in particular Macrotermitinae, Nasutitermitinae, Termitinae), for example Mastotermes sp., such as *Mastrotermes darwiniensis*, Crytotermes sp., Incistitermes sp., Kalotermes sp., such as *Kalotermes flavicollis*, Marginitermes sp., Anaconthotermes sp., Zootermopsis sp., Coptotermes sp., such as *Coptotermes formosanus*, Heterotermes sp., Psammotermes sp., Prorhinotermes sp., Schedorhinotermes sp., Allodontermes sp., Nasutitermes sp., Termes sp., Amitermes sp., Globitermes sp., Microcerotermes sp., *Oniscus asselus, Aramadium vulgare, Porcellio scaber,* Reticulitermes sp., such as *Reticulitesmes flavipes, Reticulitermes lucifugus.*

From the family of the Formicidae, for example *Atta cephalotes, Lasius niger, Lasius brunneus, Componotus ligniperda, Monomorium pharaonis, Solenopsis geminata, Monomorium minimum, Iridomyres humilis,* Dorylus sp., Exiton sp.

From the superfamily of the Vespoidea, for example, *Vespa germanica, Vespa vulgaris, Vespa media, Vespa saxonica, Vespa crabro, Vespula macalata, Polistes nympha, Vespa orintalis, Vespa mandarinia, Vespa velutina.*

From the superfamily of the Apoidea, mention may be made of the so-called killer bee.

Some of the abovementioned species are pests which cause severe damage in agriculture, in fruit growing, in forestry, in stored products and to buildings and materials, or, for example in the case of the wasps, which are at least a considerable nuisance and, in extreme cases, even health hazards (anaphylactic shock).

As a rule, the formulations according to the invention comprise between 0.0002 and 0.25% by weight, preferably between 0.001 and 0.02% by weight, in particular between 0.003 and 0.007% by weight, of silafluofen. For example, they can be in the form of an aqueous solution, suspension or emulsion, in the form of a paste or in solid form. Alternatively, the carrier can be a foodstuff of vegetable or animal origin, in particular part of a plant. As a rule, the formulations comprise at least one other component which attracts the insects, which may vary depending on the insect species to be attracted.

Insect attractant additives can be based on carbohydrates or on protein. The two principles may also be combined. Risk of spoiling may require an addition of a preservative, in particular in the case of protein-containing baits such as fish, poultry or cat feed.

In the control of wasps, liquid preparations based on water or alcohol are preferred since they can be picked up by the gathering individuals more easily and more rapidly and simultaneously satisfy the requirement of the nest for fluids. An aqueous preparation comprising, for example, corn syrup, sucrose, maltodextrin, a protein and, if appropriate, a preservative, has proven suitable as a liquid carrier for the control of wasps. Also suitable are mixtures of honey and water in which the honey, preferably real honey, attracts the gathering individuals.

Liquid preparations may additionally comprise a suitable gelling agent, such as a polysaccharide, preferably 0.5 to 10% by weight of a gelling agent.

It has proved advantageous to provide liquid formulations in an absorptive material, such as cottonwool, or to provide it to the insects from the storage container by means of a wick.

However, some ant and wasp species prefer solid or semi-solid protein-containing baits of which they bite off pieces and transport them to the nest.

Others, in turn, (for example leaf-cutting ants) prefer a vegetarian diet, so that parts of plants, such as stalks and leaves can be used for these insect species as carriers for the active substance. Carriers which have proven suitable are, for example, the leaves of taro, sweet potato, cassava and coffee.

The ready-to-use formulations (baits) are prepared by adding to the carrier a silafluofen formulation at a calculated, acutely sublethal dosage rate which is suitable for this application. Examples of suitable formulation types are the following, emulsifiable concentrates, (EC) being preferred:

a) a wettable powder which is readily dispersible in water is obtained by mixing 25 parts by weight of active substance, 65 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

b) A dispersion concentrate which is readily dispersible in water is prepared by mixing 20 parts by weight of active substance, 6 parts by weight of alkyl phenol polyglycol ether (®Tritonx207), 3 parts by weight of isotridecanol polyglycol ether (8 EO) and 71 parts by weight of paraffinic mineral oil (boiling range for example approximately 255° to above 377° C.), and grinding the mixture in a ball mill to a fineness of below 5 microns.

c) An emulsifiable concentrate can be prepared from 15 parts by weight of active substance, 75 parts by weight of cyclohexanone as solvent and 10 parts by weight of oxethylated nonylphenol (10 EO) as emulsifier.

d) Granules can be prepared from 2 to 15 parts by weight of active substance and an inert carrier material for granules, such as attapulgite, pumice granules and/or quartz sand.

The examples which follow are intended to illustrate the invention without limiting it thereto.

A: Preparation of the emulsifiable concentrate (EC) 19.6% by weight of silafluofen

| | |
|---|---|
| 19.6% by weight of | silafluofen |
| 7.5% by weight of | ® Emulsogen EL (Hoechst AG; non-ionic fatty acid polyglycol ester with 36 mol of ethylene oxide (EO)) |
| 2.9% by weight of | ® Sapogenat T200 (Hoechst AG; Tributylphenol polyglycol ether with 20 mol of EO) |
| 65.7% by weight of | ® Solvesso 200 (Exxon Chemicals) |

65.7% by weight of ®Solvesso 200 (Exxon Chemicals) were mixed for 1 hour in a stirred flask. The EC obtained in this manner was used for the biological examples which follow.

B: Biological examples
  1. Common wasp (Vespa vulgaris)
     A honey/water mixture (honey:water=1:5) was treated with 0.005% by weight of silafluofen in the form of the abovementioned EC. A wasp nest complete with 844 workers was taken from the open; in the greenhouse, the nest was placed in a secured cage which allowed the wasps to fly, and a cottonwool ball to which this mixture had been applied was used as the bait.
     All the gathering wasps on the feed source were tagged with color. The distribution of silafluofen in the wasp nest ($^{14}$C labeling) and the mortality rate were determined over 9 days at a temperature of 25° C. and a relative atmospheric humidity of 75%.

TABLE 1

Distribution of silafluofen

| Days from the beginning of the experiment | Distribution of silafluofen (ng/mg of bodyweight) | | | |
|---|---|---|---|---|
| | tagged wasps | untagged wasps | queen | larvae discarded from the nest |
| 0.1 | 50.2 | 37.1 | | |
| 1 | 40.0 | 22.2 | | |
| 2 | 13.9 | 7.0 | | 2.8 |
| 3 | 12.5 | 4.9 | | 31.5 |
| 7 | 12.7 | 1.4 | | 13.2 |
| 9 | | 0.6 | 0.14 | 7.7 |

TABLE 2

Cumulative destruction rate (%)

| Days from the beginning of the experiment | Workers % | Larvae % | Queen % |
|---|---|---|---|
| 0.1 | 8.8 | | |
| 1 | 18.9 | 2.0 | |
| 2 | 29.9 | 3.4 | |
| 3 | 37.9 | 4.9 | |
| 7 | 90.6 | 41.7 | |
| 9 | 99.1 | 47.8 | 100% |

As shown in these experiments, all adult wasps as well as the queen are destroyed by the sublethal amounts of silafluofen which are introduced. Larvae are decimated to a high degree, or are no longer sufficiently fed and die.

2. Leaf-cutting ant (*Atta cephalotes*)

Taro, sweet potato, cassava and coffee plants were sprayed with a ready-to-use aqueous silafluofen formulation prepared with the abovementioned EC, the silafluofen content of the plants being set at 0.0005% by weight of active ingredient at the outset of the experiment. These plants were fed to a colony of leaf-cutting ants (8678 individuals) for 21 days at 25° C. and a relative atmospheric humidity of 75%, more of the ready-to-use formulation was then applied to the plants up to a content of 0.0025% by weight of active ingredient, and the experiment was continued for a further 35 days.

TABLE 3

| Cumulative destruction rate (%) | |
|---|---|
| Day | % |
| 6 | 7 |
| 10 | 10 |
| 19 | 55 |
| 36 | 73 |
| 51 | 98 |
| 56 | 100 |

I claim:

1. An insecticidal formulation for controlling social insects, which insects are selected from the order of Isoptera, which formulation comprises between 0.00002% and 0.25% by weight silafluofen, and which formulation further comprises at least one additional component which attracts the insects, and a carrier therefor, the silafluofen content of the formulation being such that the formulation has no acutely lethal effect on those individual insects which pick up the formulation.

2. The formulation as claimed in claim 1, wherein the formulation comprises silafluofen as the sole insecticide.

3. The formulation as claimed in claim 1, which is prepared in a form selected from the group consisting of suspension, emulsion, paste and solid.

4. The formulation as claimed in claim 1, wherein the carrier is a foodstuff of vegetable or animal origin or a part of a plant.

5. The formulation as claimed in claim 1, wherein the carrier is essentially a honey/water mixture and whereas the honey acts as the component which attracts the insects.

6. An aqueous formulation as claimed in claim 1, which additionally comprises a gelling agent.

7. A process for controlling social insects, which insects are selected from the order of Isoptera, wherein a formulation comprising silafluofen as the sole insecticide is placed at a site which is accessible to the insects and frequently visited by them, wherein the insects pick up the formulation, transport it to their nest, and feed it to other individual insects, and wherein the formulation has a silafluofen content such that the formulation, after a time lag, destroys the individual insects which have picked up the formulation directly and/or have taken it up by feeding.

8. The process as claimed in claim 7, wherein the silafluofen content of the formulation is between 0.0002% and 0.25% by weight.

9. The process as claimed in claim 7, wherein the formulation is prepared in a form selected from the group consisting of aqueous solution, suspension, emulsion, paste and solid.

10. The process as claimed in claim 7, wherein a foodstuff of vegetable or animal origin, or a part of a plant, is used as a carrier for the formulation.

11. The process as claimed in claim 7, wherein the formulation comprises at least one additional component which attracts the insects.

12. The process as claimed in claim 10, wherein the carrier of the formulation is essentially a honey/water mixture and in which the honey acts as the component which attracts the insects.

13. The process as claimed in claim 7, whereas the formulation is water-based and wherein the formulation further comprises a gelling agent.

14. The process as claimed in claim 7, wherein the formulation is water-based and is provided in an absorptive material.

15. A process for controlling social insects, which insects are selected from the order of Isoptera, wherein a formulation according to claim 1 is placed at a site which is accessible to the insects and frequently visited by them, wherein the insects pick up the formulation, transport it to their nest, and feed it to other individual insects, and where the silafluofen content is such that the formulation, after a time lag, destroys the individual insects which have picked up the formulation directly and/or have taken it up by feeding.

16. The process as claimed in claim 15, wherein the formulation is water-based and is provided in an absorptive material.

17. The process as claimed in claim 15, wherein said formulation is prepared in a form selected from the group consisting of suspension, emulsion, paste and solid.

18. The process as claimed in claim 15, wherein the carrier is a foodstuff of vegetable or animal origin or a part of a plant.

19. The process as claimed in claim 15, wherein the carrier is essentially a honey/water mixture and whereas the honey acts as the component which attracts the insects.

20. The process as claimed in claim 15, wherein said formulation additionally comprises a gelling agent.

* * * * *